United States Patent [19]

Franetzki et al.

[11] Patent Number: 4,976,703

[45] Date of Patent: Dec. 11, 1990

[54] MEDICAL CATHETER FOR INTRAVASCULAR LONG-TERM INFUSION OF MEDICATION WITH POLYSILOXANE HYDROGEL COATING

[75] Inventors: Manfred Franetzki, Uttenreuth; Helmut Funke, Moehrendorf; Eugen Schweiker, Bubenreuth, all of Fed. Rep. of Germany

[73] Assignee: Siemens Aktiengesellschaft, Berlin and Munich, Fed. Rep. of Germany

[21] Appl. No.: 310,617

[22] Filed: Feb. 15, 1989

[30] Foreign Application Priority Data

Feb. 22, 1988 [DE] Fed. Rep. of Germany ....... 3805508

[51] Int. Cl.$^5$ .............................................. A61M 5/00
[52] U.S. Cl. .................................... 604/247; 604/265; 604/275; 604/280
[58] Field of Search ................... 604/8, 247, 265, 275, 604/280–284; 128/207.14; 285/256

[56] References Cited

U.S. PATENT DOCUMENTS

| | | | |
|---|---|---|---|
| 2,299,210 | 10/1942 | Dray | 604/275 X |
| 3,434,869 | 3/1969 | Davidson | |
| 4,375,816 | 3/1983 | Labianca | 604/8 |
| 4,548,430 | 10/1985 | Haubert et al. | 285/256 |
| 4,557,959 | 12/1985 | Kuehlein et al. | |
| 4,657,541 | 4/1987 | Iclikawa et al. | 604/408 |
| 4,675,361 | 6/1987 | Ward, Jr. | 525/92 |
| 4,705,501 | 11/1987 | Wigness et al. | |
| 4,769,016 | 9/1988 | Labianca | 604/280 |
| 4,784,160 | 11/1988 | Szilagyi | 128/784 |
| 4,801,297 | 1/1989 | Mueller | 604/280 |

FOREIGN PATENT DOCUMENTS

| | | |
|---|---|---|
| 0185865A1 | 7/1986 | European Pat. Off. . |
| 1491682 | 5/1969 | Fed. Rep. of Germany . |
| 3204762 | 2/1986 | Fed. Rep. of Germany . |
| 1417013 | 12/1975 | United Kingdom . |

Primary Examiner—John D. Yasko
Assistant Examiner—Adam J. Cermak
Attorney, Agent, or Firm—Hill, Van Santen, Steadman & Simpson

[57] ABSTRACT

A medical catheter for intravascular long-term infusion of medication by an implanted or extracorporeal dosage device characterized by the catheter tube being of a single or multi-layer elastomer having a distal end shaped such that the exit opening for the medication is laterally arranged axially offset relative to the distal end of the catheter. The catheter is also coated with an external protective layer composed of a hydrogel.

8 Claims, 2 Drawing Sheets

MEDICAL CATHETER FOR INTRAVASCULAR LONG-TERM INFUSION OF MEDICATION WITH POLYSILOXANE HYDROGEL COATING

BACKGROUND OF THE INVENTION

The present invention is directed to a medical catheter for the intravascular long-term infusion of medication by implanted or extracorporeal dosage devices, said catheter comprising a tube with a catheter tip composed of a single layer or multiple layers of elastomer, whose external protective layer is composed of a toxicologically faultless and biologically compatible elastic plastic that is soft in comparison to the layer lying therebelow.

Medical working devices which are constructed of multilayer plastic materials are disclosed in U.S. Pat. No. 4,557,959, and German Patent No. 32 04 762.

In long-term infusion of medications, for example insulin, into a body through externally wearable or implantable dosage devices, the output thereof is connected to a catheter, whose opening is preferably placed in the peritoneum and is, thus, intraperitoneally located, or into a large vein and is, thus, an intravenous insertion. Problems, that are related to a reaction of a human body to the foreign body or part, occur in such long-term catheterization. The following three reaction patterns, essentially, will occur:

(a) a connective tissue skin grows from the introduction location of the catheter into the peritoneum or, respectively, the blood vessel or from the point of contact therewith in the direction towards the catheter tip and grows around the tip;

(b) a connective tissue grows in a distal direction proceeding from the catheter tip; and (c) body cells, macromolecules and tissue particles penetrate into the catheter opening and agglomerate to the walls thereof.

The adhesion of such growth depends, to a particular degree, on the surface roughness. The foreign body reactions are triggered by stimuli of a chemical nature, first by the material alien to the body itself and, secondly, by the infused liquid. Over and above this, a mechanical irritation also occurs, for instance due to the stiffness in the edge of the catheter and this stiffness acts as a trigger. Nothing is known regarding the share of the aforementioned irritative or stimuli effects in the foreign body reaction. However, the growth rate is frequently far faster than the useful life of the implanted dosage device so that a premature function outage with the necessity of a surgical catheter revision will occur.

European Patent No. 0 185 865 discloses an implantable intraperitoneal catheter that, among other things, is suitable for injection of insulin into the human body. In order to avoid blockage due to growth of the body tissue, the catheter tip is provided with exit holes arranged following one another between which disk-shaped spacer elements that project laterally are situated. A particular disadvantage of this known arrangement is that the lateral projecting spacer disk first make the introduction of the catheter more difficult and can injure the inside wall of the vessel during the introduction procedure. A second problem is that it causes vascular growth behind the projecting spacer elements in the stationary condition due to eddy formations of the blood stream in a flowing direction.

U.S. Pat. No. 4,705,501 discloses a catheter of the above-known type, whose distal end can be opened and closed by an inflowing liquid or, respectively, by the counter-pressure of the liquid flowing in the vessel. To this end, the distal end of the catheter is bevelled at such an acute angle that a movable tongue arranged between the obtuse angle of the bevel and the acute angle thereof opens or closes the catheter, dependent on the respective flow conditions. Given catheters that are connected to a dosage pump, such a valve mechanism is superfluous.

U.S. Pat. No. 3,434,869, which was the basis for German Offenlegungsschrift 14 91 682, discloses a method for manufacturing catheters having an improved physiological compatibility, whose surfaces are coated with a layer composed of organo-polysiloxane elastomer. Such a polysiloxane elastomer has silica gel as a filler material. It has been shown that this material reacts with the tissue and blood so that proteins, thrombocytes and, due to the relative rough surface, connecting tissue, as well, will adsorbe thereon.

SUMMARY OF THE INVENTION

The object of the present invention is to provide a catheter such that its function time is noticeably lengthened and optimally exceeds the service life of the implanted dosage device.

This object is achieved by an improvement in a medical catheter for intravascular long-term infusion of medication by a dosage device including implanted and extracorporeal dosage devices, said catheter comprising a catheter tube and a catheter tip composed of a single or multi-layer elastomer, whose external protective layer is composed of a toxilogically faultless and biologically compatible elastic plastic that is soft in comparison to the layer lying therebelow and have a smooth surface. The improvements include that the exit opening for the medication is laterally arranged axially offset relative to the distal end of the catheter and an outer protective layer applied to the completely fabricated catheter.

The axial offset of the medication exit opening relative to the catheter tip provides that the catheter closure, due to growth of body tissue beginning from the catheter tip, is at least considerably retarded. The subsequent coating of the catheter with the protective layer rounds off sharp edges and points. Further, the film has a smooth surface. Overgrowth of tissue are, thus, greatly reduced.

Further improvements of the service life give simultaneous stabilization of the catheter tip can be achieved by constructing the distal end of the catheter to be closed by a hollow cylindrical closure member having a rounded head part and a lateral medication exit opening situated in said closure member, said closure member having an outer surface of a material selected from a group consisting of titanium, titanium nitride, titanium carbide and of pyrolytic carbon. The member may be a plastic member coated with materials selected from this group or be a solid member of a material selected from the group. Preferably, the lateral opening is conically expanded toward the outside proceeding from the axial interior and the outer surfaces are polished to be microscopically smooth.

To hold the rounded tip onto the catheter, it is desirable to use a pinch ring which, preferably, is of an x-ray opaque material. This enables x-ray observation of the placing of the catheter tip.

In another embodiment of the invention, the catheter tip is composed of elastic plastic material and has means forming or providing emergency exit openings for medication exit, when a main exit opening is plugged, said means comprising lateral openings in the shape of longitudinally extending slots. This embodiment has the advantage that no interruptions of the medication delivery occurs, even after the exit opening has potentially grown shut. The longitudinal slots arranged at the circumference of the catheter tip can spread apart due to the pressure increase inside the catheter and due to the tangential force thereby produced, so that the medication finds a path towards the outside.

British Patent No. 1,417,013, in fact, discloses that a catheter tip can be provided with lateral slots as medication exit openings for the introduction of medication into the vessel to be catheterized. These slots, however, do not serve the purpose of enabling an emergency exit of the medication given a blockage of the main delivery opening. On the contrary, they have the function of valves in order to prevent a back-flow of the body fluid through the catheter towards the outside.

Other features and advantages of the present invention will be readily apparent from the following description of the preferred embodiments, the drawings and claims.

DESCRIPTION OF THE PREFERRED EMBODIMENTS

Figure 1:
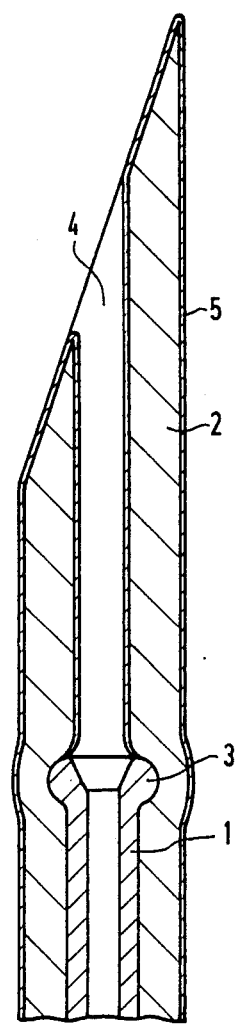
FIG. 1 is a longitudinal cross sectional view of a tip of a full plastic catheter in accordance with the present invention.

The principles of the present invention are particularly useful when incorporated in a catheter tip for a catheter tube, which is not shown in greater detail and can be either composed of a silicone tube filled with an x-ray contrast agent or of a polyethylene tube or a composite tube having an inside tube of polyethylene and outside jacket of silicone. The catheter shown in FIG. 1 is such a composite tube wherein the elastomer tube 2 of silicone is slipped onto a core tube 1 of polyethylene. To that end, the end of the core tube 1 is provided with an annular bead 3 that prevents the slipped-on silicone tube 2 from being stripped off of the tube 1. The tip of the silicone tube 2 is cut off at an acute angle of approximately 15°. What is thereby achieved is that, first, the catheter tip becomes very soft and, thus, will present less mechanical irritation for the body tissue and also the distal catheter opening 4 has an axial spacing from the tip with the result that a catheter blockage is at least retarded, given potential growth of the body tissue proceeding from the tip. In order to achieve a better biologically compatibility and also in order to manufacture a smooth surface, the catheter is coated with a protective layer 5 of hydrogel, for example polyethylene glycol. The coating can be produced by immersion of the completely fabricated catheter into the polyethylene glycol. Such a hydrogel film has a smooth surface and contains no fillers. What is simultaneously achieved therewith is that the sharp edges and points that arose when cutting the silicone tube are rounded or smoothed off. Instead of a polyethylene glycol, other soft and body-compatible materials, such as filler-free polysiloxane, can also be used for the coating.

Figure 2:
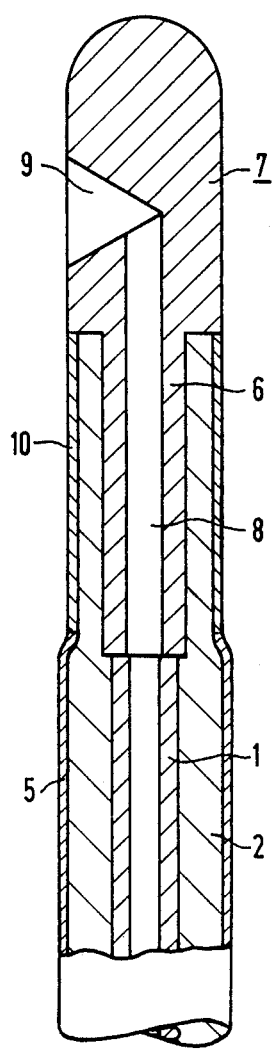
FIG. 2 is a longitudinal cross section of a catheter tip having a distal, separate closure member in accordance with the present invention.

An embodiment of the catheter tip is illustrated in FIG. 2. The silicone tube 2 is slipped onto the distal end of the core tube 1 of the catheter to project by a certain amount. A hollow cylindrical closure member 7 having a rounded head part has a shaft or neck portion 6 which is introduced into this projecting part. This closure member comprises an inside bore 8 that emerges at right angles into a lateral or radially extending opening 9 that is conically expanded from inside towards the outside and merges with the outer surface of the head 7 at an axially inward spaced position from the distal end of the closure member. The closure member, including the conical opening 9, is composed of biologically compatible material, such as a material selected from a group consisting of titanium, titanium nitride, titanium carbide or pyrolytic carbon, as a solid material, or is a plastic material which is coated with a material selected from this group. The surface of the member, whether it is the solid member or a coated member, is polished to a high gloss to provide a microscopically smooth polished surface.

A ring part 10 can serve for compression-proof and tensile fastening of the closure member 7 in the projecting part of the silicone tube 2. This ring part 10 is slipped onto the silicone tube 2 that is pinched in an anti-slip fashion against the shaft portion 6 of the closure member 7. The ring part is composed of a mechanically stable, biocompatible material, preferably of the same material as the closure member 7. The surface of the ring part 10 is polished to a high gloss corresponding to the closure member. Given a selection of an x-ray opaque material for the ring part and for the closure member 7, this can, thus, also, simultaneously, serve the purpose of identifying the respective position of the catheter tip under x-ray observation.

Figure 3:
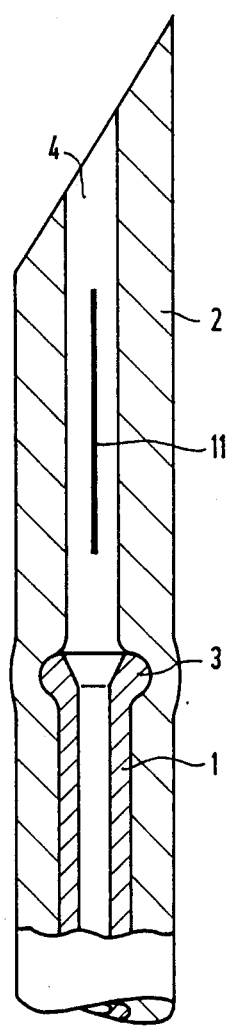
FIG. 3 is a longitudinal cross sectional view of a catheter tip similar to the tip of FIG. 1 having lateral slots as emergency openings.
Figure 4:
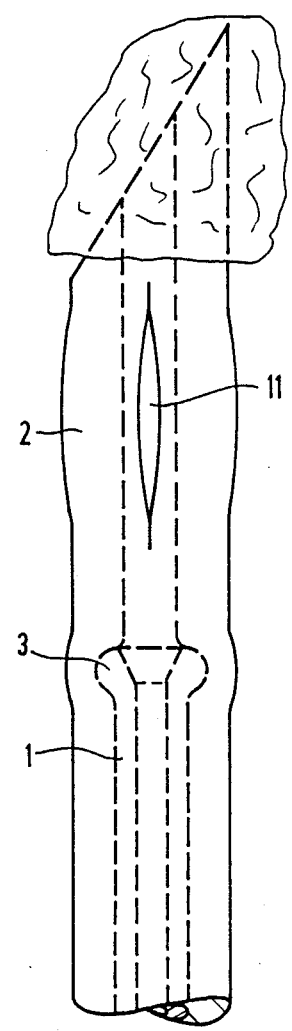
FIG. 4 is a side view of the tip of FIG. 3 illustrating the opening of the slots acting as emergency openings.

In FIGS. 3 and 4, a modification of the catheter tip of FIG. 1 is illustrated. In this modification, a longitudinal slot 11 is introduced into the silicone tube 2 at an inward position relative to the distal end of the catheter opening 4. These longitudinal slots 11 are means forming an emergency opening and open under pressure of a pumped medication, given a potential closure of the distal opening 4 by an overgrowth tissue, as illustrated in FIG. 4. What is thereby achieved is that the medication delivery is not interrupted, even when such a closure emergency operating property that considerably lengthens its service life.

Although various minor modifications may be suggested by those versed in the art, it should be understood that we wish to embody within the scope of the patent granted hereon all such modifications as reasonably and properly come within the scope of our contribution to the art.

We claim:

1. In a medical catheter for intravascular long-term infusion of medications by a dosage device, said medical catheter comprising a catheter tube having a longitudinal axis and a catheter tip at a distal end thereof, said tube being composed of a single layer or multiple layers of elastomer having an external protective surface layer having a smooth surface and being composed of a toxicologically faultless and biologically compatible elastic plastic material that is soft in comparison to the material lying therebelow, the improvements comprising an exit opening for the medication being arranged offset along the longitudinal axis relative to the distal end of the catheter tip and the external protective layer being composed of a hydrogel and being applied to the completely fabricated catheter, said hydrogel being a polysiloxane free of a filler.

2. In a medical catheter according to claim 1, wherein the catheter tip is composed of elastic plastic material and additionally has means for forming emergency exit openings for medication exit given a plugging of the main exit opening, said means being lateral openings in the shape of longitudinal slots axially spaced inward from the main exit opening.

3. In a medical catheter according to claim 1, wherein the distal end of the catheter tube is closed with a hollow cylindrical closure member having a rounded head part and said exit opening being a radially extending opening situated on a cylindrical surface of said closure member, said closure member being connected to the catheter tube by a ring part slipped onto the catheter tube, said closure member and said ring part having outer surfaces composed of a material selected from a group consisting of titanium, titanium nitride, titanium carbide and pyrolytic carbon and said closure member and ring part being polished microscopically smooth.

4. In a medical catheter according to claim 3, wherein the exit opening is conically expanded towards the outside surface of the closure member.

5. In a medical catheter according to claim 4, wherein said ring part is made of x-ray opaque material.

6. In a medical catheter according to claim 3, wherein a part of the catheter tip composed of elastic plastic material has means for providing emergency openings for medication exit when the main exit opening in the closure member is plugged, said means being lateral openings in the shape of longitudinal extending slots axially inward from the closure member.

7. In a medical catheter according to claim 3, wherein said ring part is made of x-ray opaque material.

8. In a medical catheter according to claim 1, wherein the catheter tip consists of the distal end of the catheter tube which is cut off at an acute angle to the longitudinal axis to form the exit opening axially spaced from the distal end.

* * * * *